United States Patent [19]

Lang et al.

[11] Patent Number: 4,886,879
[45] Date of Patent: Dec. 12, 1989

[54] PROCESS FOR THE PREPARATION OF TRIFLUORODICHLOROETHYL-SUBSTITUTED ACIDS AND ZINC COMPOUNDS

[75] Inventors: Robert W. Lang, Pratteln, Switzerland; Bernd Klingert, Inzlingen, Fed. Rep. of Germany

[73] Assignee: Ciba-Geigy Corporation, Ardsley, N.Y.

[21] Appl. No.: 176,580

[22] Filed: Apr. 1, 1988

Related U.S. Application Data

[62] Division of Ser. No. 835,481, Mar. 3, 1986, Pat. No. 4,759,881.

[30] Foreign Application Priority Data

Mar. 11, 1985 [CH]  Switzerland ................ 1090/85

[51] Int. Cl.$^4$ ................................................ C07F 3/06
[52] U.S. Cl. .................................... 540/486; 556/128; 556/119; 547/3; 548/402; 546/11
[58] Field of Search ................. 556/128, 119; 546/11; 540/486; 548/402; 549/3

[56] References Cited

U.S. PATENT DOCUMENTS 3,290,333  12/1966  Fainberg et al. ................ 556/128
3,755,395  8/1973  Bakassian et al. ................ 556/128

OTHER PUBLICATIONS

Journal of Fluorine Chemistry, vol. 34, (1986), 241-250—Hemer.

*Primary Examiner*—John Doll
*Assistant Examiner*—Stuart L. Hendrikson
*Attorney, Agent, or Firm*—Stephen V. O'Brien

[57] ABSTRACT

Zinc compounds of formula II

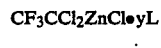 $CF_3CCl_2ZnCl\cdot yL$  (II)

wherein y is 1 or 2 and L is a solvent ligand selected from the group of the N-disubstituted acid amides, N-substituted lactams and the organic sulfoxides, are suitable for reaction with $CO_2$, COS or $SO_2$ to give, after working up, the acids of formula I

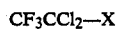 $CF_3CCl_2—X$  (I)

wherein X is $—CO_2H$, $—CSOH$ or $—SO_2H$, in good yield.

4 Claims, No Drawings

PROCESS FOR THE PREPARATION OF TRIFLUORODICHLOROETHYL-SUBSTITUTED ACIDS AND ZINC COMPOUNDS

This is a divisional of application Ser. No. 835,481 filed on Mar. 3, 1986, now U.S. Pat. No. 4,759,881.

The present invention relates to a process for the preparation of 2,2,2-trifluoro-1,1-dichloroethylcarboxylic, -thiocarboxylic and -sulfinic acid using adducts of 2,2,2-trifluoro-1,1-dichlorozinc chloride with a solvent and to said adducts.

Adducts of 2,2,2-trifluoro-1,1-dichloroethyl zinc chloride with ethers, e.g. dioxane and tetrahydrofuran, are known from U.S. patent specification No. 3 290 333. In Collection Czechoslov. Chem. Commun., Vol. 37, pp. 3946–3349 (1972), A. Posta and O. Paleta teach that the reaction of an adduct of 2,2,2-trifluoro-1,1-dichlorozinc chloride and dioxane with an acetyl chloride, in contrast to the same reaction with a perfluoroalkyl zinc chloride, does not yield the expected ketone. Our own investigations showed that the described zinc chloride adducts are also unable to react with carbon dioxide. This result is confirmed in J.C.S. Chem. Comm., pp. 885–886 (1976), where it is shown that not even perfluoroalkyl zinc iodides react with carbon dioxide. J. Fluorine Chemistry 22, p. 585, (1983) teaches that perfluoroalkyl iodides are reacted with $CO_2$, in the presence of zinc and dimethylformamide as solvent, to perfluoroalkylcarboxylic acids when the reaction is carried out under ultrasonic irradiation.

It is an object of the present invention to provide a process for the preparation of trifluorodichloroethyl-substituted acids of formula I

$$F_3C-CCl_2-X \qquad (I)$$

wherein X is $-COOH$, $-C(S)OH$ or $-SO_2H$, by reacting an organometal compound with $CO_2$, $COS$ or $SO_2$, in the presence of an inert solvent, and subsequent hydrolysis, which process comprises using a zinc compound of formula II

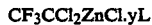

$$CF_3CCl_2ZnCl.yL \qquad (II)$$

as organometal compound, wherein y is 1 or 2 and L is a solvent ligand selected from the group of the N-disubstituted acid amides, N-substituted lactams and organic sulfoxides.

It is preferred to use $SO_2$ and, most particularly, $CO_2$, in the process of this invention for the preparation of 2,2,2-trifluoro-1,1-dichlorosulfinic acid and 2,2,2-trifluoro-1,1-dichloropropionic acid.

The zinc compounds of formula II are novel and also constitute an object of the present invention.

In formula II, L as an N-disubstituted acid amide is preferably a carboxamide, in particular one of the formula

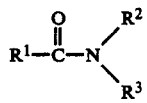

wherein $R^1$ is a hydrogen atom, alkyl of 1 to 12, preferably 1 to 4, carbon atoms, which is unsubstituted or substituted by halogen, preferably by fluorine or chlorine, or is cycloalkyl containing 4 to 7 ring carbon atoms which is unsubstituted or substituted by $C_1$–$C_4$alkyl or halogen, or is alkenyl or 2 to 12, preferably 2 to 4, carbon atoms, phenyl, benzyl or $-NR^2R^3$, where $R^2$ and $R^3$ are each independently of the other $C_1$–$C_{12}$alkyl, cycloalkyl containing 5 or 6 ring carbon atoms, or $R^2$ and $R^3$, when taken together, are tetramethylene or pentamethylene, each of which may be interrupted by $-O-$, $-S-$ or $-NR^4$ ($R^4=C_1$–$C_4$alkyl).

$R^1$ is preferably a hydrogen atom or methyl. $R^2$ and $R^3$ are preferably methyl or ethyl.

Examples of acid amides are dimethylformamide, diethylformamide, dimethylacetamide, tetramethylurea and N-formylpyrrolidine. Dimethylformamide is particularly preferred.

L as N-substituted lactam preferably has the formula

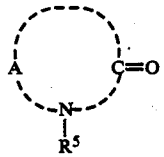

wherein A is dimethylene, trimethylene, tetramethylene or pentamethylene, and $R^5$ is $C_1$–$C_{12}$alkyl, preferably $C_1$–$C_4$alkyl, cyclohexyl or cyclopentyl. $R^5$ is preferably methyl or ethyl. Examples of such lactams are N-methylpropiolactam, N-methylpyrrolidone, N-ethylpyrrolidone, N-methylpiperidinone, N-methyl-ε-caprolactam, with N-methylpyrrolidone being preferred.

L as an organic sulfoxide corresponds preferably to the formula

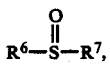

$$R^6-\overset{O}{\underset{\|}{S}}-R^7,$$

wherein each of $R^6$ and $R^7$ independently of the other is $C_1$–$C_{12}$alkyl, preferably $C_1$–$C_4$alkyl, or $R^6$ and $R^7$, when taken together, are tetramethylene or pentamethylene. Examples of organic sulfoxides are: dimethyl sulfoxide, methylethyl sulfoxide, diethyl sulfoxide, tetramethylene sulfoxide and pentamethylene sulfoxide.

Preferred zinc compounds of formula II are those in which L is an N-disubstituted carboxamide. In formula II, y is preferably 2. A particularly preferred zinc compound is $CF_3CCl_2ZnCl.2$ dimethylformamide.

The zinc compounds of formula II are prepared in a manner known per se by the direct reaction of zinc, preferably in the form of zinc dust, with 1,1,1-trifluoro-2,2,2-trichloroethane excluding air and moisture and in an inert solvent. It is advantageous to cool the reaction mixture. The zinc compounds of this invention can then be isolated in conventional manner by removing the solvent or by crystallisation.

Another preparatory method comprises dissolving the known ether adducts of $CF_3CCl_2ZnCl$ (q.v. U.S. patent specification No. 3 290 333) in a solvent L and heating the solution to about 100° C., whereupon the adducts of the invention are formed by ligand exchange and can then be isolated in known manner.

The zinc compounds of this invention are crystalline compounds which are stable when air and moisture are excluded. It is surprising that the zinc compounds of the invention react with $CO_2$, $COS$ and $SO_2$. It is possible, but not necessary, to apply ultrasonic irradiation. The desired acids are formed in good yield and excellent purity. The process is particularly economic owing to the use of inexpensive starting materials.

The process of the invention is preferably carried out in an inert polar aprotic solvent. Illustrative of such solvents are in particular ethers, tertiary amines, sulfones and solvents corresponding to the ligand L. Typical solvents are: dimethyl ether, diethyl ether, dibutyl ether, dioxane, tetrahydrofuran, ethylene glycol dimethyl or diethyl ether, diethylene glycol dimethyl ether, triethylene glycol dimethyl ether, dimethyl sulfone, tetramethylene or pentamethylene sulfone, trimethylamine, triethylamine, methyl diethylamine, tripropylamine, tributylamine, N-methylmorpholine, N-methylpiperidine, N-methylpyrrolidine, pyridine and N-methylpyrrole.

The inert solvent is preferably an N-disubstituted acid amide, an N-substituted lactam or an organic sulfoxide. Most preferably, the ligand and the solvent are identical. The most preferred solvent is dimethylformamide. Another embodiment of the process comprises using zinc compounds of formula II, wherein y is 2 and L is dimethylformamide.

An advantageous embodiment of the process comprises using a solvent corresponding to the ligand L and preparing the zinc compound II in situ by reacting $CF_3CCl_3$ with zinc and then carrying out the reaction with $CO_2$, COS or $SO_2$.

The process of the invention is conveniently carried out in the temperature range from 0° to 50° C., preferably at room temperature. The process can be carried out under normal pressure or under over-pressure, e.g. in an autoclave, and the pressure may be up to about 100 bar, preferably up to 50 bar.

To isolate the acids, the reaction mixture is subjected to hydrolysis. The hydrolysis is conveniently carried out with a dilute mineral acid, e.g. hydrochloric acid or sulfuric acid, which is suitably mixed with ice to cool the reaction mixture. After the hydrolysis, the resultant acids may be extracted with a suitable solvent, e.g. diethyl ether. The solvent is then removed by distillation to yield the desired acids, which may in turn be purified by distillation.

It has proved expedient to isolate the zinc salts which have formed during the reaction before hydrolysing the reaction mixture. The zinc salts are obtained as crystalline solids and can be readily isolated by crystallisation. This is done by removing the solvent and recrystallising the residue from a suitable solvent. The zinc salts may correspond to the formulae $(CF_3CCl_2Y)_2Zn \cdot yL$ or $(CF_3CCl_2Y)ZnCl \cdot yL$ wherein Y is —C(O)O—, —C(S)O— or —S(O)O—. The acids can be obtained from the zinc salts by hydrolysis.

The acids obtained by the process of this invention may be suitably used as esterification catalysts or for the preparation of surface-active compounds, of oil and water repellants and of plant protective agents (q.v. German Offenlegungschrift 1 900 758).

The following Examples illustrate the invention in more detail. The reactions are carried out with the exclusion of moisture and in an inert gas atmosphere (nitrogen or argon).

EXAMPLE 1

Preparation of $CF_3CCl_2ZnCl \, (SL)_n$ complexes 65.4 g (1 mole) of zinc dust (activated according to Fieser & Fieser) are suspended in a solvent (SL) in a 1 liter three-necked flask and then 188 g (1 mole) of $CF_3CCl_3$ are slowly added (see Table 1 for amount of solvent, reaction time and reaction temperature). The reaction mass is subsequently filtered at the indicated reaction temperature over "Selecta" filter flakes and the complexes precipitate in crystalline from the cold filtrate or upon cooling the filtrate. When using dimethylformamide (DMF) as solvent, the complexes are precipitated by adding diethyl ether ($Et_2O$). The complexes are further purified by recrystallisation from the respective solvent and, if the solvent employed is dimethylformamide, from $EtO_2$. The solvent is removed by decantation and the colourless crystalline residue is dried in vacuo. The yields are 70–80%. The results are reported in Table 1.

TABLE 1

| Complex | Amount of solvent | Reaction time (hours) | Reaction temperature | melting point (°C.) |
|---|---|---|---|---|
| $CF_3CCl_2ZnCl$ (dioxane) | 500 ml | 3 | 101° C. | 173 |
| $CF_3CCl_2ZnCl$ ($Et_2O$) | 800 ml | 20 | room temperature | 105 |
| $CF_3CCl_2ZnCl$ $(THF)_2$* | 800 ml | 3 | room temperature | 135 |
| $CF_3CCl_2ZnCl$ $(DME)_1$** | 800 ml | 3 | room temperature | 68 |
| $CF_3CCl_2ZnCl$ $(DMF)_2$ | 500 ml | 2 | room temperature | 67 |

*tetrahydrofuran, **dimethoxyethane

EXAMPLE 2

Preparation of $CF_3CCl_2ZnCl \, (DMF)_2$ by ligand exchange reaction 4.0 g (12 mmols) of of $CF_3CCl_2ZnCl$ ($EtO_2$) are dissolved at room temperature in 50 ml of $EtO_2$. With efficient stirring, 2 ml (26 mmols) of dimethylformamide are slowly added and after a time a two-phase system forms, with the DMF complex settling in oily form as lower phase. After a few minutes this complex begins to crystallise. The crystals are isolated by decantation, washed with $EtO_2$ and then dried in vacuo (yield: >95%).

EXAMPLE 3

Preparation of 1,1,1-trifluoro-2,2-dichloropropionic acid by the single vessel process 65.4 g (1 mole) of zinc dust (activated according to Fieser & Fieser) are suspended in 500 ml of dimethylformamide in a three-necked flask and then 188 g (120 ml; 1 mole) of $CF_3CCl_3$ which has been freshly dried over a molecular sieve and subsequently distilled are added slowly to this suspension. After a few minutes the zinc begins to dissolve and the reaction mixture exotherms. The reaction temperature is kept below 30° C. by external cooling. The batch is then stirred for 1 hour and filtered over "Selecta" filter flakes (available from Schleicher & Schüll). With efficient stirring, $CO_2$ gas is bubbled into the clear, reddish brown filtrate over a frit for 6 hours. Initially strong absorption occurs. Then the solution is poured into a mixture of 500 ml of 10% aqueous HCl and 300 g of ice and extracted with 5×300 ml of $EtO_2$. The combined extracts are washed with 200 ml of 2% aqueous HCl, dried over $MgSO_4$ and concentrated by rotary evaporation at room temperature. The residual brown liquid is distilled at 26 mbar, the acid being obtained at 62°–64° C. as a colourless liquid (yield: 50%). The pure acid solidifies at room temperature and has a melting point of 25°–30° C.

EXAMPLE 4

Preparation of 1,1,1-trifluoro-2,2-dichloropropionic acid starting from isolated $CF_3CCl_2ZnCl(SL)_n$ complexes In a 1 liter three-necked flask, 1 mole of each of the complexes listed in Table 1 is dissolved at room temperature in 500 ml of dimethylformamide and the solution is treated with $CO_2$ gas and worked up as described in Example 3. The isolated acid is obtained in yields from 35–50%.

EXAMPLE 5

Preparation of $(CF_3CCl_2COO)_2Zn(DMF)$

In a 90 ml glass autoclave, 35 ml of dimethylformamide (DMF) are added to 16.4 g (50 mmols) of $CF_3CCl_2ZnCl(EtO_2)$ with efficient stirring. Then $CO_2$ gas is introduced under pressure and the conditions are kept constant for 24 hours at 5.0 bar and 40° C. When the reaction is complete, the solvent is stripped off under high vacuum at room temperature and the yellow resinous residue is digested with ether. The residual solid is recrystallised from acetone, affording 8.2 g (62%) of colourless needles with a melting point of 188° C. Hydrolysis as performed in Example 3 yields the free acid.

EXAMPLE 6

Preparation of $CF_3CCl_2SO_2ZnCl(DMF)$

The procedure of Example 5 is repeated, introducing $SO_2$ instead of $CO_2$ gas and maintaining a pressure of 2.2 bar over 24 hours at 40° C. The solvent is stripped off under reduced pressure and the residual solid is digested with ether, affording 12.2 g (53%) of colourless crystals with a melting point of 100°–110° C. Hydrolysis as performed in Example 3 yields the free sulfinic acid.

What is claimed is:

1. A zinc compound of formula II $$CF_3CCl_2ZnCl.yl \qquad (II)$$

wherein y is 1 or 2 and L is a solvent ligand selected from the group consisting of dimethylformamide, diethylformamide, dimethylacetamide, tetramethylurea, N-formylpyrrolidine, N-methylpropiolactam, N-methylpyrrolidone, N-ethylpyrrolidone, N-methylpiperidone, N-methyl-ε-caprolactam, dimethyl sulfoxide, methylethyl sulfoxide, diethyl sulfoxide, tetramethylene sulfoxide and pentamethylene sulfoxide.

2. A zinc compound according to claim 1, wherein L is selected from the group consisting of dimethylformamide, diethylformamide and dimethylacetamide.

3. A zinc compound according to claim 1, wherein y is 2.

4. A zinc compound according to claim 1 of the formula $CF_3CCl_2ZnCl.2$ dimethylformamide.

* * * * *